United States Patent [19]
de Nanteuil et al.

[11] Patent Number: 5,591,728
[45] Date of Patent: Jan. 7, 1997

[54] NEW PHOSPHONIC ACID COMPOUNDS

[75] Inventors: Guillaume de Nanteuil, Suresnes; Georges Remond, Versailles; Tony Verbeuren, Vernouillet, all of France

[73] Assignee: Adir Et Compagnie, Courbevoie, France

[21] Appl. No.: 497,811

[22] Filed: Jul. 3, 1995

Related U.S. Application Data

[62] Division of Ser. No. 267,971, Jun. 29, 1994, Pat. No. 5,481,030.

[30] Foreign Application Priority Data

Jun. 30, 1993 [FR] France ................... 93 07927

[51] Int. Cl.⁶ ............ A61K 31/675; A61K 31/66
[52] U.S. Cl. .................... 514/80; 514/121
[58] Field of Search ............ 514/80, 121, 221

[56] References Cited

FOREIGN PATENT DOCUMENTS 0122840 12/1989 European Pat. Off. .

OTHER PUBLICATIONS

Yanmei, et al. Phosphorous, Sulfur Silicon Relat. Flem. (1993) 78(1–4) 15–21.
Bertenshaw, et al. J. Med. Chem. (1993), 36(1) 173–6.
Bertenshaw, et al., *J. Med. Chem.* (Jan. 8, 1993) 36(1), 173–76.

*Primary Examiner*—Joseph Conrad
*Attorney, Agent, or Firm*—The Firm of Gordon W. Hueschen

[57] ABSTRACT

Compound of formula (I):

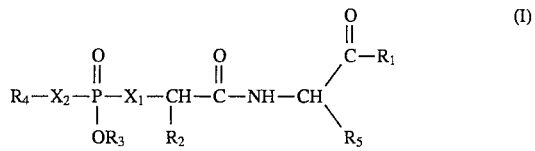

in which:
- $R_1$ represents a hydroxyl, alkoxy or amino (unsubstituted or substituted) group,
- $R_2$ represents an unsubstituted or substituted alkyl group,
- $X_1$ represents —NH—,
- $X_2$ represents —O—,
- $R_3$ represents a hydrogen atom or an alkyl or phenyl group,
- $R_4$ represents an alkyl group which is always substituted with one or more hydroxyl, benzyloxy, benzyloxycarbonylamino, amino, mono- or dialkylamino, acetoxy or 2,2-dimethyl-1,3-dioxolan-4-yl groups, such groups being identical or different,
- $R_5$ represents a 3-indolylmethyl, naphthylmethyl, alkyl, phenyl or benzyl group, its isomers as well as its addition salts with a pharmaceutically acceptable acid or base, and medicinal products containing the same are useful as endothelin convertase inhibitor.

5 Claims, No Drawings

NEW PHOSPHONIC ACID COMPOUNDS

The present application is a division of our prior-filed application Ser. No. 08/267,971, filed Jun. 29, 1994, now U.S. Pat. No. 5,481,030, issued Jan. 2, 1996.

The present invention relates to new phosphonic acid compounds.

Endothelins are peptides of 21 amino acids having very potent vasoconstrictor activity. These endothelins are synthesized from a precursor, big endothelin, by an enzyme known as "endothelin converting enzyme" or proendothelin convenase. This enzyme belongs to the metalloprotease class, and it may be inhibited by phosphoramidon. An increase in plasma endothelin levels has been demonstrated in disorders such as hypertension, angina, myocardial infarction, renal insufficiency, shock, diabetes, hypercholesterolemia, cerebral vasospasm, Raynaud's disease, inflammatory arthritis, cardiac insufficiency and pulmonary hypertension. It has hence been postulated that endothelin might play a part in peripheral and myocardial ischemia, hypertension, renal insufficiency, hypoxic pulmonary vasoconstriction, asthma, atherosclerosis and arthritis. It was hence of special interest to synthesize substances that inhibit proendothelin convenase.

The prior state of the art is illustrated, in particular, by Patents EP0,518,299 and WO 92/01,468.

The invention relates more especially to the compounds of formula (I):

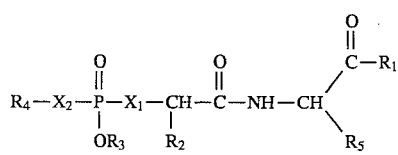

in which:

$R_1$ represents a hydroxyl or linear or branched ($C_1$–$C_6$) alkoxy group or an amino group (unsubstituted or substituted with 1 or 2 linear or branched ($C_1$–$C_6$) alkyl groups), $R_2$ represents a linear or branched ($C_1$–$C_6$) alkyl group, unsubstituted or substituted with a phenyl or ($C_3$–$C_7$) cycloalkyl group, $X_1$ represents —NH—, $X_2$ represents —O—, $R_3$ represents a hydrogen atom, a linear or branched ($C_1$–$C_6$) alkyl group or a phenyl group, $R_4$ represents a linear or branched ($C_1$–$C_6$) alkyl group which is always substituted with one or more hydroxyl, benzyloxy, benzyloxycarbonylamino, amino, linear or branched ($C_1$–$C_6$) mono- or dialkylamino, acetoxy or 2,2-dimethyl-1,3-dioxolan-4-yl groups, such groups being identical or different, $R_5$ represents a 3-indolylmethyl, naphthylmethyl or linear or branched ($C_1$–$C_6$) alkyl group or a phenyl or benzyl group, their enantiomers, diastereoisomers and epimers as well as their addition salts with a pharmaceutically acceptable acid or base.

Among pharmaceutically acceptable bases, there may be mentioned, without implied limitation, sodium hydroxide, potassium hydroxide, lithium hydroxide, triethylamine, tert-butylamine, and the like.

Among pharmaceutically acceptable acids, there may be mentioned, without implied limitation, hydrochloric, sulfuric, tartaric, maleic, fumaric, methanesulfonic, camphoric, and the like, acids.

The invention also encompasses the process for preparing the compounds of formula (I), wherein the amino acid of the formula (II), in racemic form or the form of a pure enantiomer:

in which:

$R'_1$ represents a linear or branched ($C_1$–$C_6$) alkoxy group or an amino group (unsubstituted or substituted with 1 or 2 linear or branched ($C_1$–$C_6$) alkyl groups), and $R_5$ has the same meaning as in the formula (I), is used as starting material, which compound is reacted with a compound of formula (III), in racemic form or the form of a pure enantiomer:

in which $R_2$ and $X_1$ have the same meaning as in the formula (I) and P represents a suitable protective group, to yield a compound of formula (IV), the isomers of which, where appropriate, are separated according to a standard separating technique:

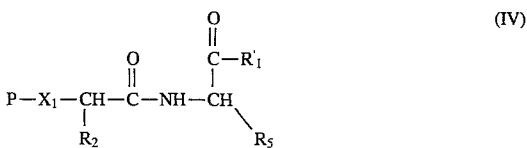

in which $R'_1$, $R_2$, $X_1$, $R_5$ and P have the same meaning as above, which is deprotected, depending on the nature of P, by a suitable technique, to yield the compound of formula (V):

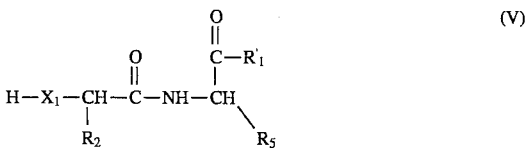

in which $R'_1$, $R_2$, $R_5$ and $X_1$ have the same meaning as above, which is reacted:

in an inert medium. at room temperature, with a chloroform solution prepared beforehand by stirring the following in an inert medium:

one equivalent of a phenyl dichlorophosphate of formula (VII):

one equivalent of the compound of formula (VIII):

in which $X_2$ has the same meaning as in the formula (I), $R'_4$ represents an alkyl group (substituted with one or more benzyloxy. benzyloxycarbonylamino, acetoxy or linear or branched ($C_1$–$C_6$) dialkylamino or 2,2-dimethyl-1,3-dioxolan-4-yl groups).

and two equivalents of triethylamine.
to yield, after deprotection in a basic medium, the compound of formula (I/a), a special case of the compounds of formula (I):

$$R''_4-X_2-\underset{\underset{OH}{|}}{\overset{\overset{O}{\|}}{P}}-X_1-\underset{\underset{R_2}{|}}{CH}-\overset{\overset{O}{\|}}{C}-NH-CH\underset{\diagdown R_5}{\diagup \overset{\overset{O}{\|}}{C}-R'_1} \quad (I/a)$$

in which $R'_1$, $R_2$, $R_5$ and $X_2$ have the same meaning as above and $R''_4$ represents an alkyl group (substituted with one or more hydroxyl, benzyloxy, benzyloxycarbonylamino, acetoxy or linear or branched ($C_1$–$C_6$) dialkylamino or 2,2-dimethyl-1,3-dioxolan-4-yl groups), in which compound of formula (I/a) the group $R''_4$ may be converted, when the latter represents:

an alkyl group substituted with one or more benzyloxy groups, to an alkyl group substituted with one or more hydroxyl groups, by catalytic hydrogenation, an alkyl group substituted with one or more acetoxy groups, to an alkyl group substituted with one or more hydroxyl groups, by reaction with lithium hydroxide or sodium hydroxide, which compound of formula (I/a):

may be subjected to conversion of the group $R'_1$ therein when the latter represents an alkoxy group to a corresponding hydroxyl group, may be purified according to standard purification techniques, may be subjected to separation of its isomers according to standard separating techniques, and may be convened to a corresponding salt of an acid or base.

The process for preparing the compounds of formula (I) also encompasses the synthesis of the reference compound, phosphoramidon of formula:

Phosphoramidon was hitherto isolated from strains of Streptomyces tanashiensis (Tet. Lett. 43, 97–100, 1972).

The subject of the present invention is also pharmaceutical compositions containing as active principle at least one compound of general formula (I) or one of its addition salts with a pharmacologcally acceptable acid, alone or in combination with one or more nontoxic, inert excipients or vehicles.

Among the pharmaceutical compositions according to the invention, there may be mentioned more especially those which are suitable for oral, parenteral or nasal administration, simple or sugar-coated tablets, sublingual tablets, hard gelatin capsules, troches, suppositories, creams, ointments, skin gels, and the like.

The dosage varies according to the patient's age and weight and the nature and severity of the complaint, as well as the administration route.

The latter may be oral, nasal, rectal or parenteral. Generally speaking, the unit dosage ranges between 0.1 and 1,000 mg for a treatment administered in 1 to 3 doses per 24 hours.

The examples which follow illustrate the invention but in no way limit it. The starting materials used in the examples are known starting materials or are prepared according to known procedures.

The abbreviations used in the examples are as follows:

| | |
|---|---|
| Leu | in place of the leucine residue |
| Trp | in place of the tryptophan residue |
| Et | in place of ethyl |
| Val | in place of the valine residue |
| Ile | in place of the isoleucine residue |
| cyclohexylAla | in place of the cyclohexylalanine residue |
| tert-butylGly | in place of the tert-butylglycine residue |
| Phe | in place of the phenylalanine residue |
| Nal | in place of the 2-naphthylalanine residue |

EXAMPLE 1:
N-[(2,3-Dihydroxypropoxy)hydroxyphosphinyl]-(S)Leu-(S)Trp-OH disodium salt Stage A: N-[(2,3-Diacetoxypropoxy)phenoxyphosphinyl]-(S)Leu-(S)Trp-OEt 4.8 mmol of 2,3-diacetoxypropanol dissolved in anhydrous chloroform are added at 0°–5° C. to a mixture containing 4.8 mmol of phenyl dichlorophosphate and 9.6 mmol of triethylamine in anhydrous chloroform. The resulting mixture is stirred for 3 hours at room temperature. A solution containing 4.8 mmol of (S)Leu-(S)Trp-OEt in anhydrous chloroform (prepared by peptide coupling, according to the technique described by W. KONIG and R. GEIGER (Ber, 103, 788, 1970) of Z-Leu-OH and H-Trp-OEt) is then added to the above mixture. After 48 hours of stirring at room temperature, the reaction mixture is washed with water and then with saturated sodium chloride solution, dried, filtered and evaporated under vacuum. The oil obtained is purified by chromatography on a silica colunto using a dichloromethane/ethyl acetate (70:30) mixture, and yields the expected product.

Stage B: N-[(2,3-Dihydroxypropoxy)hydroxyphosphinyl]-(S)Leu-(S) Trp-OH disodium salt The product obtained in Stage A is saponified in a mixture containing 1.75 ml of 1N sodium hydroxide and 20 ml of ethanol cooled to 0°–5° C. After evaporation of the ethanol, the residual oil is diluted with water, washed several times with dichloromethane and then lyophilized. The lyophilizate is purified by passage through a SEPHADEX (LH-20) column. The combined aqueous phases are lyophilized again.

Yield: 50% Mass spectrum: FAB: $[M+Na]^+$: m/z=538

EXAMPLE 2:
N-[(2-Benzyloxyethoxy)hydroxyphosphinyl]-(S)Leu-(S)Trp-OH disodium salt The expected product is obtained according to the process described in Example 1 by replacing 2,3-diacetoxypropanol in Stage A by 2-benzyloxyethanol.

Mass spectrum: FAB: $[M+H]^+$: m/z=576

EXAMPLE 3:
N-[(2-Hydroxyethoxy)hydroxyphosphinyl]-(S)Leu-(S)Trp-OEt disodium salt The expected product is obtained by catalytic hydrogenation of 2.7 mmol of the compound obtained in Stage A of Example 2, at atmospheric pressure and at room temperature, in the presence of 50 ml of ethanol, 230 mg of sodium bicarbonate and 6 ml of water and of a (50:50) PtO$_2$-Pd/C10% mixture as catalysts. After 48 hours of hydrogenation, the catalysts are filtered off and the solution is evaporated. The residual oil is taken up with water, washed with dichloromethane and lyophilized. The lyophilizate is then dissolved in water, purified on a SEPHADEX (LH-20) column and then lyophilized again, and yields the expected product.

Mass spectrum: FAB: [M+H]$^+$: m/z=492

EXAMPLE 4:
N-[(2-Hydroxyethoxy)hydroxyphosphinyl]-(S)Leu-(S)Trp-OH disodium salt The expected product is obtained by catalytic hydrogenation of the compound described in Example 2 using the method described in Example 3.

Mass spectrum: FAB: [M+H]$^+$: m/z=486

EXAMPLE 5:
N-[(3-Hydroxypropoxy)hydroxyphosphinyl]-(S)Leu-(S)TrP-OH dilithium salt The expected product is obtained according to the process described in Example 1 by replacing 2,3-diacetoxypropanol in Stage A by 3-acetoxypropanol and by saponification using lithium hydroxide.

Mass spectrum: FAB: [M+H]$^+$: m/z=468

Example 6: N-[[2-(Benzyloxycarbonylamino)ethoxy]hydroxyphosphinyl]-(S)Leu-(S) Trp-OEt dilithium salt The expected product is obtained according to the process described in Example 1 by replacing 2,3-diacetoxypropanol in Stage A by 2-(benzyloxycarbonylamino)ethanol. The saponification is carried out using lithium hydroxide.

Mass spectrum: FAB: [M+H]$^+$: m/z=609

Example 7: N-{[(2,2-Dimethyl-1,3-dioxolan-4-yl)methoxy]hydroxy-phosphinyl}-(S)Leu-(S) Trp-OEt, sodium salt Stage A: N-{[(2,2-Dimethyl-1,3-dioxolan-4-yl)methoxy]phenoxyphosphinyl}-(S)Leu-(S) Trp-OEt The expected product is obtained according to the process described in Stage A of Example 1 by replacing 2,3-diacetoxypropanol by 2,2-dimethyl-1,3-dioxolane-4-methanol.

Stage B: N-{[(2,2-Dimethyl-1,3-dioxolan-4-yl) methoxy]hydroxyphosphinyl}-(S)Leu-(S) Trp-OEt sodium salt A solution containing 63 mmol of sodium bicarbonate in 5 ml of water is added to a solution containing 63 mmol of the compound obtained in the preceding stage in 30 ml of ethanol. The medium is hydrogenated for 48 hours at room temperature in the presence of platinum oxide as catalyst under a pressure of 1,200 mbar. After the catalyst has been filtered off and the solvent evaporated off, the residue is taken up with 50 ml of water. After the aqueous phase has been washed with ethyl acetate and filtered, the expected product is obtained after lyophilization.

Mass spectrum: FAB: [M+H]$^+$: m/z=562 Infrared (Nujol): $\delta_{co}$ ester=1728 cm$^{-1}$ $\delta_{co}$ amides=1653 cm$^{-1}$

EXAMPLE 8:
N-{[(1-Hydroxymethyl-2-hydroxy)ethoxy]hydroxyphosphinyl]-(S)Leu-(S) Trp-OH dilithium salt The expected product is obtained according to the process described in Example 5 by replacing 3-acetoxypropanol in Stage A by 1,3-diacetoxy-2-propanol.

Mass spectrum: FAB: [M+H]$^+$: m/z=484

EXAMPLE 9: N-[(3-Aminopropoxy)hydroxyphosphinyl]-(S)Leu-(S)Trp-OEt lithium salt Stages A and B: N-{[(3-Benzyloxycarbonylamino)propoxy]hydroxyphosphinyl}-(S)Leu-(S) Trp-OEt lithium salt The expected product is obtained according to the process described in Example 6 by replacing (benzyloxycarbonylamino)ethanol in Stage A by (benzyloxycarbonylamino)propanol.

Stage C: N-[(3-Aminopropoxy)hydroxyphosphinyl]-(S)Leu-(S)Trp-OEt lithium salt

The expected product is obtained after catalytic hydrogenation of the compound described in the preceding stage using palladium/charcoal as catalyst, at room temperature, at a pressure of 1,200 mbar, followed by lyophilization.

Mass Spectrum: FAB: [M+2H-Li]$^+$: m/z=483

EXAMPLE 10:
N-[((R)-2,3-Dihydroxypropoxy)hydroxyphosphinyl]-(S)Leu-(S)Trp-OH dilithium salt The expected product is obtained according to the process described in Example 1 by replacing 2,3-diacetoxypropanol in Stage A by the isomer (R)-2,3-diacetoxypropanol and by saponification using lithium hydroxide.

Mass Spectrum: FAB: [M+H]$^+$: m/z=484

EXAMPLE 11:
N-[((S)-2,3-Dihydroxypropoxy)hydroxyphosphinyl]-(S)Leu-(S)Trp-OH dilithium salt The expected product is obtained according to the process described in Example 1 by replacing 2,3-diacetoxypropanol in Stage A by the isomer (S)-2,3-diacetoxypropanol and by saponification using lithium hydroxide.

Mass Spectrum: FAB: [M+H]$^+$: m/z=484

EXAMPLE 12:
N-[(3,4-Dihydroxybutoxy)hydroxyphosphinyl]-(S)Leu-(S) Trp-OH dilithium salt The expected product is obtained according to the process described in Example 1 by replacing 2,3-diacetoxypropanol in Stage A by 3,4-diacetoxybutanol and by saponification using lithium hydroxide.

Mass spectrum: FAB: [M+H]$^+$: m/z=498

EXAMPLE 13:
N-(1-Hydroxymethyl-3-hydroxypropoxy)hydroxyphosphinyl](S)Leu-(S)Trp-OH dilithium salt The expected product is obtained according to the process described in Example 1 by replacing 2,3-diacetoxypropanol in Stage A by 1-acetoxymethyl-3-acetoxypropanol and by saponification using lithium hydroxide.

Mass spectrum: FAB: [M+H]$^+$: m/z=498

EXAMPLE 14:
N-(2,4-Hydroxybutoxy)hydroxyphosphinyl-(S)Leu-(S) Trp-OH dilithium salt The expected product is obtained according to the process described in Example 1 by replacing 2,3-diacetoxypropanol in Stage A by 2,4-diacetoxybutanol and by saponification using lithium hydroxide.

Mass spectrum: FAB: $[M+H]^+$: m/z=498

EXAMPLE 15:
N-[(2,3,4-Trihydroxybutoxy)hydroxyphosphinyl]-(S)Leu-(S) Trp-OH dilithium salt The expected product is obtained according to the process described in Example 1 by replacing 2,3-diacetoxypropanol in Stage A by 2,3,4-triacetoxybutanol and by saponification using lithium hydroxide.

Mass spectrum: FAB: $[M+H]^+$: m/z=514

EXAMPLE 16:
N-[(2,3-Dihydroxypropoxy)hydroxyphosphinyl]-(S)Leu-(S) TrP-OEt sodium salt The expected product is obtained according to the process described in Example 7 using 2,3-diacetoxypropanol in Stage A.

EXAMPLE 17:
N-[(2,3-Dihydroxypropoxy)hydroxyphosphinyl]-(S) Val-(S) Trp-OH dilithium salt The expected product is obtained according to the process described in Example 1 by replacing (S)Leu-(S)Trp-OEt in Stage A by (S)Val-(S)Trp-OEt and by saponification using lithium hydroxide.

Mass spectrum: FAB: $[M+H]^+$: m/z=470

EXAMPLE 18:
N-[(2,3-Dihydroxypropoxy)hydroxyphosphinyl]-(S)Ile-(S) Trp-OH dilithium salt The expected product is obtained according to the process described in Example 1 by replacing (S)Leu-(S)Trp-OEt in Stage A by (S)Ile-(S)Trp-OEt and by saponification using lithium hydroxide.

Mass spectrum: FAB: $[M+H]^+$: m/z=484

EXAMPLE 19:
N-[(2,3-Dihydroxypropoxy)hydroxyphosphinyl]-(S)cyclohexylAla-(S)TrP-OH dilithium salt The expected product is obtained according to the process described in Example 1 replacing (S)Leu-(S)Trp-OEt in stage A by (S)cyclohexylAla-(S)Trp-OEt and by saponification using lithium hydroxide.

Mass spectrum: FAB: $[M+H]^+$: m/z=524

EXAMPLE 20:
N-[(2,3-Dihydroxypropoxy)hydroxyphosphinyl]-(S)tert-butylGly-(S)Trp-OH dilithium salt The expected product is obtained according to the process described in Example 1 by replacing (S)Leu-(S)Trp-OEt in Stage A by (S)tert-butylGly-(S)Trp-OEt and by saponification using lithium hydroxide.

Mass spectrum: FAB: $[M+H]^+$: m/z=484

EXAMPLE 21:
N-[(2,3-Dihydroxypropoxy)hydroxyphosphinyl]-(S)Leu-(S)tert-butylGly-OH dilithium salt The expected product is obtained according to the process described in Example 1 by replacing (S)Leu-(S)Trp-OEt in Stage A by (S)Leu-(S)tert-butylGly-OEt and by saponification using lithium hydroxide.

Mass spectrum: FAB: $[M+H]^+$: m/z=411

EXAMPLE 22:
N-[(2,3-Dihydroxypropoxy)hydroxyphosphinyl]-(S)Leu-(S)Phe-OH dilithium salt The expected product is obtained according to the process described in Example 1 by replacing (S)Leu-(S)Trp-OEt in Stage A by (S)Leu-(S)Phe-OEt and by saponification using lithium hydroxide.

Mass spectrum: FAB: $[M+H]^+$: m/z=445

EXAMPLE 23:
N-[(2,3-Dihydroxypropoxy)hydroxyphosphinyl]-(S)Leu-(S)Nal-OEt sodium salt The expected product is obtained according to the process described in Example 1 by replacing (S)Leu-(S)Trp-OEt in Stage A by (S)Leu-(S)Nal-OEt and by saponification using lithium hydroxide.

Mass spectrum: FAB: $[M+H]^+$: m/z=495

EXAMPLE 24: Phosphoramidon disodium salt (N-[α-(S)-(rhamnopyranosyloxy)hydroxyphosphinyl]-(S)leu-(S) Trp-OH disodium salt)

The expected product is obtained according to the process described in Example 1 by replacing 2,3-diacetoxypropanol in Stage A by rhamnose triacetate. The isomers obtained are then separated and purified by chromatography on a reversed-phase silica column ($C_{18}$) using water as eluent. The expected product possesses the same physicochemical properties as that of commercial phosphoramidon.

Mass spectrum: FAB: $[M+H]^+$: m/z=588 Optical rotation: $\alpha_D^{20}$=−30.1 (c=0.96%, water)

Pharmacological Study of the Compounds of the Invention

EXAMPLE 25: In vivo study of the compounds of the invention on pithed rats

Sprague-Dawley rats (300400 g) are anesthetized with ether. The animals are then pithed and placed under artificial respiration. The vagus nerves are sectioned and the carotid arteries ligated. A catheter is introduced into one of the carotid arteries to measure arterial blood pressure. A second catheter is introduced into the vein of the penis to enable substances to be injected.

After a stabilization period, the animals receive an injection of endothelin-1 (ET-1; 0.5 nmol/kg) or its precursor, big endothelin-1 (big ET-1; 1 nmol/kg). The pressor responses are recorded and, after the pressure has returned to its initial value (1 h 30 min to 2 hours), a second injection of ET-1 or of big ET-1 is given in the presence or absence of an infusion of a product of the invention or of the reference substance, phosphoramidon. Phosphoramidon and the products of the invention had no effect on ET-1-induced hypertension. In contrast, they inhibited big ET-1-induced pressor responses in a dose-dependent manner, indicating an inhibition of ECE.

The results for IC$_{50}$ values of these substances with respect to big ET-1 are collated below.

| Example | IC$_{50}$ (μg/kg/min) |
|---|---|
| 1 | 100 |
| 3 | 280 |
| 4 | 430 |
| 8 | 480 |
| 9 | 200 |
| 10 | 230 |
| 11 | 100 |
| 12 | 140 |
| Phosphoramidon | 125 |

EXAMPLE 26: In vitro study of the compounds of the invention on perfused isolated rat kidney The studies are performed on kidneys prepared from male Wistar rats (300400 g). The rats are anesthetized with pentobarbitone sodium (50 mg/kg i.p.) and the left kidney is prepared so as to permit perfusion with Tyrode solution. The variations in perfusion pressure are measured continuously. The perfusion flow rate is 6 ml/min. After stabilization, a bolus injection of ET- 1 (0.03 nmol) or of big ET-1 (0.4 nmol) is performed and the pressor response is recorded. After the pressure has returned to the baseline value, a second injection of ET-1 or of big ET-1 is carried out, either in a control solution, or in the presence of phosphoramidon or one of the products of the invention. None of the products had an effect on the pressor responses to ET-1. In contrast, phosphoramidon and the compounds of the invention substantially inhibited the pressor responses obtained with big ET-1. The IC$_{50}$ values of the products are calculated and the results are given in μM.

| Example | IC$_{50}$ (μM) |
|---|---|
| 1 | 4 |
| 3 | 5 |
| 4 | 7 |
| Phosphoramidon | 0.9 |

EXAMPLE 27: Pharmaceutical composition

Composition formula for 1,000 tablets containing a 10 mg dose

| Compound of Example 1 | 10 g |
|---|---|
| Hydroxypropylcellulose | 2 g |
| Wheat starch | 10 g |
| Lactose | 100 g |
| Magnesium stearate | 3 g |
| Talc | 3 g |

We claim:

1. A method for treating a mammal afflicted with a condition requiring an endothelin convertase inhibitor comprising the step of administering to the mammal an amount of a compound selected from those of formula (I):

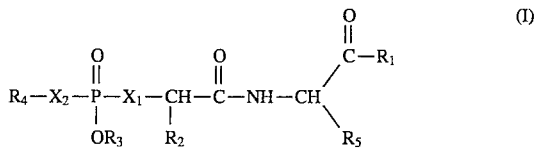

in which:

R$_1$ represents hydroxyl, linear or branched (C$_1$–C$_6$) alkoxy, or amino which is unsubstituted or substituted with 1 or 2 linear or branched (C$_1$–C$_6$) alkyl, R$_2$ represents linear or branched (C$_1$–C$_6$) alkyl, unsubstituted or substituted with phenyl or C$_3$–C$_7$ cycloalkyl, X$_1$ represents —NH—, X$_2$ represents —O—, R$_3$ represents hydrogen, linear or branched (C$_1$–C$_6$) alkyl, or phenyl, R$_4$ represents linear or branched (C$_1$–C$_6$) alkyl which is substituted with one or more hydroxyl, benzyloxy, benzyloxycarbonylamino, amino linear or branched (C$_1$–C$_6$) mono- or dialkylamino, acetoxy, or 2,2-dimethyl-1,3-dioxolan-4-yl, such groups being identical or different, R$_5$ represent 3-indolylmethyl, naphthylmethyl, linear or branched (C$_1$–C$_6$) alkyl, phenyl, or benzyl, its enantiomers, diastereosiomers and epimers as well as its addition salts with a pharmaceutically-acceptable acid or base, which is effective for alleviation of said condition.

2. A method of claim 1, wherein R$_4$ represents (C$_1$–C$_6$) alkyl which is substituted with one or more hydroxyl, or an enantiomer, diastereoisomer, or epimer thereof or an addition salt thereof with a pharmaceutically-acceptable acid or base.

3. A method of claim 1, wherein R$_5$ represents 3-indolylmethyl, or an enantiomer, diastereoisomer, or epimer thereof, or an addition salt thereof with a pharmaceutically-acceptable acid or base.

4. A method of claim 1 wherein the compound is N-[2, 3-dihydroxypropoxy)hydroxyphosphinyl]-(S)Leu-(S)Trp-OH, an isomer thereof, or an addition salt thereof with a pharmaceutically-acceptable acid or base.

5. A method of claim 1 wherein the compound administered is in the form of a pharmaceutical composition in which it is present together with one or more pharmaceutically-acceptable excipients or vehicles.

* * * * *

UNITED STATES PATENT AND TRADEMARK OFFICE
CERTIFICATE OF CORRECTION

PATENT NO. : 5,591,728
DATED : January 7, 1997
INVENTOR(S) : Guillaume de Nanteuil et al.

It is certified that error appears in the above-indentified patent and that said Letters Patent is hereby corrected as shown below:

Column 1, ln 12: "convenase" should read -- convertase --.

Column 1, ln 24: "convenase" should read -- convertase --.

Column 2, ln 19: "(HI)" should read -- (III) --.

Column 2, ln 65: "benzyloxy." should read -- benzyloxy, --

Column 2, ln 67: "groups)." should read -- groups), --.

Column 3, ln 1: "triethylamine." should read -- triethylamine, --.

Column 3, ln 2: replace "medium." with -- medium, --.

Column 3, ln 3: replace "of formula (I/a)." with -- of formula (I/a), --.

Column 3, ln 13: replace "hydroxyl." with -- hydroxyl, --.

Column 3, ln 13: replace "benzyloxy." with -- benzyloxy, --.

UNITED STATES PATENT AND TRADEMARK OFFICE
CERTIFICATE OF CORRECTION

PATENT NO. : 5,591,728
DATED : January 7, 1997
INVENTOR(S) : Guillaume de Nanteuil et al.

Page 2 of 3

It is certified that error appears in the above-indentified patent and that said Letters Patent is hereby corrected as shown below:

Column 3, ln 33: "convened" should read -- converted --.

Column 5, ln 34: "Example" should read -- EXAMPLE 6 --.

Column 5, ln 35: Delete "6" from the beginning of the line.

Column 5, ln 44: "Example 7:" should read -- EXAMPLE 7: -- and it should be on a separate line.

Column 6, ln 18: "Stage  C:" should read -- Stage C: --.

Column 6, ln 61: insert -- - -- (dash) after "phosphinyl]".

Column 7, ln 51: "TrP" should read -- Trp --.

Column 8, ln 51: "(300400 g)" should read -- (300-400 g) --

Column 9, ln 22: "(300400 g)" should read -- (300-400 g) --
   Pg. 12, ln 14

Column 9, ln 28: "retumed" should read -- returned --.

UNITED STATES PATENT AND TRADEMARK OFFICE
CERTIFICATE OF CORRECTION

PATENT NO. : 5,591,728
DATED : January 7, 1997
INVENTOR(S) : Guillaume de Nanteuil et al.

Page 3 of 3

It is certified that error appears in the above-indentified patent and that said Letters Patent is hereby corrected as shown below:

Column 10, ln 27: insert a -- , -- after "amino".

Column 10, ln 40: insert a -- , -- after "thereof".

Signed and Sealed this

Fifteenth Day of April, 1997

Attest:

BRUCE LEHMAN

Attesting Officer

Commissioner of Patents and Trademarks